United States Patent [19]

McGredy

[11] Patent Number: Plant 5,426

[45] Date of Patent: Apr. 2, 1985

[54] ROSE PLANT 'MACHADEN'

[76] Inventor: Samuel D. McGredy, 130 B Beach Rd., Castor Bay, Auckland 9, New Zealand

[21] Appl. No.: 518,088

[22] Filed: Jul. 28, 1983

[51] Int. Cl.[3] ..... A01H 5/00

[52] U.S. Cl. ..... Plt./21

[58] Field of Search ..... Plt./21

*Primary Examiner*—James R. Feyrer

*Attorney, Agent, or Firm*—Vincent G. Gioia

[57] ABSTRACT

A new red hybrid tea rose variety.

1 Drawing Figure

The present invention relates to a new and distinct variety of rose plant of the hybrid tea rose class, which was originated by my crossing as seed parent the rose known as "Karma" and the rose known as "Arturo Toscanini" as pollen parent. The denomination of this new rose is "Machaden".

Among the novel characteristics possessed by this new variety which distinguish it from its parents and all other varieties of which I am aware are its relatively large, heavily petaled, currant red flowers borne almost always one to a stem and with a pleasant old rose fragrance. The flowers open flat but the imbricate form is attractive. The plant is vigorous and tall growing. Asexual reproduction by budding of the new variety as performed in Kern County, Calif., shows that the foregoing and other distinguishing characteristics come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Colour Chart (R.H.S.C.C.). The terminology used in color description herein refers to plate numbers in the aforementioned color chart, e.g., "46A" is plate 46A of The Royal Horticultural Society Colour Chart.

Parentage: Seedling.
*Seed parent.*—"Karma".
*Pollen parent.*—"Arturo Toscanini".
Class: Hybrid Tea.

The following observations are made of specimens grown under glass in Kern County, Calif., during the month of June.

FLOWER

Blooming habit: Continuous.
Bud:
(1) *Size.*—Large.
(2) *Form.*—Pointed.
(3) *Color.*—After sepals divide, buds are currant red.
(4) *Sepals.*—Longer than bud, few appendages.
(5) *Peduncle.*—Length — long. Aspect — upright. Strength — erect. Color — near 182A.
Bloom:

(1) *Size.*—Average size when fully expanded — about 4 to 5 inches
(2) *Borne.*—Singly, one to a stem.
(3) *Form.*—High centered becoming flat upon opening, perfectly imbricate at maturity.
(4) *Petalage.*—Number of petals under normal conditions — about 50 to 60.
(5) *Color.*—The flower appears essentially currant red 46A and 46B and the color holds upon flower opening until late aging when there is some bluing to near 60A. At point of petal attachment petals are near 19A.
Petals:
(1) *Texture.*—Thick.
(2) *Appearance.*—Inside velvety, outside satiny.
(3) *Form.*—Acuminate.
(4) *Arrangement.*—Imbricated.
(5) *Petaloids in center.*—Few (5 to 10).
(6) *Persistence.*—Drop off cleanly.
(7) *Fragrance.*—Pleasant, old rose.
(8) *Lasting quality.*—Long lasting quality on plant and as cut flower.

REPRODUCTIVE ORGANS

Stamens, filaments and anthers:
*Arrangement and color.*—Many short stamens regularly arranged around styles; filaments 40D, anthers 16B.
Pollen:
*Color.*—Near 16A.
Styles: Many, short, tightly bunched, near 52B.
Stigmas:
*Color.*—Near 16C, small stigmatic area.
Hips: Globular, large, few set, near 45A, seeds do not protrude.

PLANT

Form: Tall, slightly spreading.
Growth: Vigorous, uniform long stems.
*Height attained.*—About 7 feet.
Foliage: Compound 5 leaflets.
(1) *Size.*—Large.
(2) *Quantity.*—Abundant.
(3) *Color.*—New foliage: Upper side — near to 182A. Under side — near to 183D. Old foliage: Upper side — near 137A. Under side — near to 148D.
(4) *Shape.*—Oval, long pointed.
(5) *Texture.*—Upper side is waxy and under side is satiny.
(6) *Edge.*—Serrate.

(7) *Serration.*—Small, light.

(8) *Leaf stem.*—Color — near to 182A. Under side — near 144B.

(9) *Stipules.*—Slightly bearded, long.

(10) *Resistance to disease.*—Blackspot — excellent. Mildew — good. Rust — good.

Wood:

(1) *New wood.*—Color — near 183D. Bark — smooth, waxy.

(2) *Old wood.*—Color — near 137C. Bark — smooth.

Thorns:

(1) *Thorns.*—Quantity (main stalk) — few. On laterals from stalk — average. Form — thin, slight recurve. Length — short. Color — near 145C. Position — irregular.

(2) *Prickles.*—Few on main stem, profuse on laterals.

Winter hardiness: Needs winter protection in severe climate.

I claim:

1. A new and distinct variety of rose plant of the hybrid tea rose class, substantially as shown and described, characterized particularly by relatively large, heavily petaled currant red flowers borne one to a stem on a vigorous, tall growing plant.

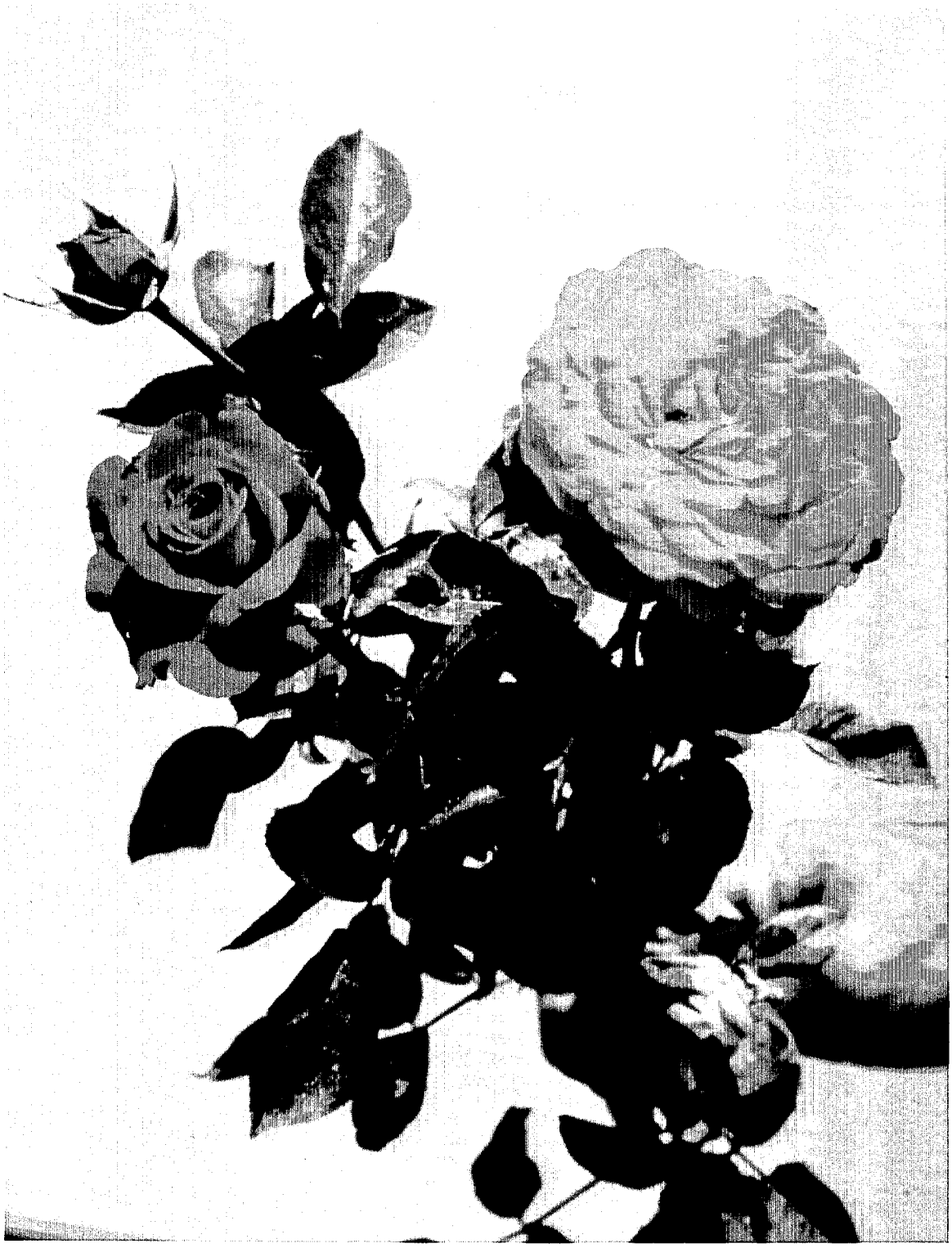

* * * * *